US008923982B2

(12) United States Patent
Howard

(10) Patent No.: US 8,923,982 B2
(45) Date of Patent: *Dec. 30, 2014

(54) LEADS WITH X-RAY FLUORESCENT CAPSULES FOR ELECTRODE IDENTIFICATION AND METHODS OF MANUFACTURE AND USE

(71) Applicant: Boston Scientific Neuromodulation Corporation, Valencia, CA (US)

(72) Inventor: Joshua Dale Howard, North Hollywood, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/258,941

(22) Filed: Apr. 22, 2014

(65) Prior Publication Data
US 2014/0228921 A1 Aug. 14, 2014

Related U.S. Application Data

(63) Continuation of application No. 13/787,171, filed on Mar. 6, 2013, now Pat. No. 8,744,596.

(60) Provisional application No. 61/617,922, filed on Mar. 30, 2012.

(51) Int. Cl.
*A61N 1/05* (2006.01)
*A61N 1/36* (2006.01)

(52) U.S. Cl.
CPC .......... *A61N 1/0534* (2013.01); *A61N 1/36128* (2013.01)
USPC .......................................... 607/115; 607/116

(58) Field of Classification Search
None
See application file for complete search history.

(56) References Cited

U.S. PATENT DOCUMENTS 3,825,787 A 7/1974 Doolittle
4,602,624 A 7/1986 Naples et al.
(Continued)

FOREIGN PATENT DOCUMENTS

EP 0580928 A1 2/1994
EP 0650694 B1 7/1998
(Continued)

OTHER PUBLICATIONS

International Search Report and Written Opinion for International Patent Application No. PCT/US2013/029324 mailed May 7, 2013.

(Continued)

*Primary Examiner* — Brian T Gedeon
(74) *Attorney, Agent, or Firm* — Lowe Graham Jones PLLC; Bruce E. Black

(57) ABSTRACT

An implantable lead for an electrical stimulation system includes a lead body having a distal end, a proximal end, a longitudinal length, and a circumference; a plurality of electrodes disposed along the distal end of the lead body in an electrode array; a plurality of terminals disposed along the proximal end of the lead body; a plurality of conductors electrically coupling the plurality of electrodes to the plurality of terminals; and at least one capsule including an x-ray fluorescent material and disposed along the distal end of the lead body relative to the electrode array to indicate, when viewed fluoroscopically, an orientation of the electrode array. The plurality of electrodes includes a plurality of segmented electrodes. Each of the plurality of segmented electrodes extends partially around the circumference of the lead body.

20 Claims, 5 Drawing Sheets

(56) References Cited

U.S. PATENT DOCUMENTS

| | | | |
|---|---|---|---|
| 4,630,611 A | 12/1986 | King | |
| 4,744,370 A | 5/1988 | Harris | |
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,322,559 B1 | 11/2001 | Daulton et al. | |
| 6,510,347 B2 | 1/2003 | Borkan | |
| 6,556,873 B1 | 4/2003 | Smits | |
| 6,564,078 B1 | 5/2003 | Marino et al. | |
| 6,678,564 B2 | 1/2004 | Ketterl et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,292,890 B2 | 11/2007 | Whitehurst et al. | |
| 7,489,971 B1 | 2/2009 | Franz | |
| 7,668,601 B2 | 2/2010 | Hegland et al. | |
| 7,761,985 B2 | 7/2010 | Hegland et al. | |
| 7,809,446 B2 | 10/2010 | Meadows | |
| 7,840,188 B2 | 11/2010 | Kurokawa | |
| 7,848,802 B2 | 12/2010 | Goetz et al. | |
| 7,856,707 B2 | 12/2010 | Cole | |
| 7,860,570 B2 | 12/2010 | Whitehurst et al. | |
| 7,974,705 B2 | 7/2011 | Zdeblick et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,225,504 B2 | 7/2012 | Dye et al. | |
| 8,295,944 B2 | 10/2012 | Howard et al. | |
| 8,321,025 B2 | 11/2012 | Bedenbaugh | |
| 8,323,277 B2 | 12/2012 | Vilims | |
| 8,473,074 B2 | 6/2013 | North et al. | |
| 8,560,085 B2 | 10/2013 | Moffitt et al. | |
| 8,583,237 B2 | 11/2013 | Bedenbaugh | |
| 8,649,879 B2 | 2/2014 | DiGiore et al. | |
| 8,688,235 B1 | 4/2014 | Pianca et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0150036 A1 | 6/2007 | Anderson | |
| 2007/0203546 A1 | 8/2007 | Stone et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2009/0187222 A1 | 7/2009 | Barker | |
| 2009/0204192 A1 | 8/2009 | Carlton et al. | |
| 2009/0276021 A1 | 11/2009 | Meadows et al. | |
| 2010/0036468 A1 | 2/2010 | Decre et al. | |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0039590 A1 | 2/2014 | Moffitt et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 1999055411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2009025816 A1 | 2/2009 |
| WO | 2009102536 A1 | 8/2009 |
| WO | 2010126877 A1 | 11/2010 |
| WO | 2013162775 A2 | 10/2013 |
| WO | 2014018092 A1 | 1/2014 |

OTHER PUBLICATIONS

U.S. Appl. No. 14/189,671, filed Feb. 25, 2014.
U.S. Appl. No. 14/173,593, filed Feb. 5, 2014.
U.S. Appl. No. 14/286,940, filed May 23, 2014.
U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,829, filed May 23, 2014.
U.S. Appl. No. 14/469,214, filed Aug. 26, 2014.
U.S. Appl. No. 14/286,797, filed May 23, 2014.

LEADS WITH X-RAY FLUORESCENT CAPSULES FOR ELECTRODE IDENTIFICATION AND METHODS OF MANUFACTURE AND USE

CROSS-REFERENCE TO RELATED APPLICATIONS

This application is a continuation of U.S. patent application Ser. No. 13/787,171 filed Mar. 6, 2013 which claims the benefit under 35 U.S.C. §119(e) of U.S. Provisional Patent Application Ser. No. 61/617,922 filed on Mar. 30, 2012, all of which are incorporated herein by reference.

FIELD

The invention is directed to the area of electrical stimulation systems and leads and methods of making and using the systems and leads. The present invention is also directed to electrical stimulation leads having electrodes and x-ray fluorescent capsules for identifying the orientation of one or more of the electrodes, as well as methods of making and using the leads, electrodes, and electrical stimulation, systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation, of neighboring neural tissue, potentially resulting in undesired side effects.

BRIEF SUMMARY

One embodiment is an implantable lead for an electrical stimulation system including a lead body having a distal end, a proximal end, a longitudinal length, and a circumference; a plurality of electrodes disposed along the distal end of the lead body in an electrode array; a plurality of terminals disposed along the proximal end of the lead body; a plurality of conductors electrically coupling the plurality of electrodes to the plurality of terminals; and at least one capsule including an x-ray fluorescent material and disposed along the distal end of the lead body relative to the electrode array to indicate, when viewed fluoroscopically, an orientation of the electrode array. The plurality of electrodes includes a plurality of segmented electrodes. Each of the plurality of segmented electrodes extends partially around the circumference of the lead body.

Another embodiment is a stimulation system comprising the lead described above and a control module coupleable to the lead and configured and arranged for providing stimulation to the plurality of electrodes of the lead.

Yet another embodiment is a method for making an implantable lead. The method includes disposing a plurality of electrodes along a distal end of a lead body and arranged in an electrode array. The plurality of electrodes includes a plurality of segmented electrodes. Each of the plurality of segmented electrodes extends partially around a circumference of the lead body. The method further includes disposing a plurality of terminals along a proximal end of the lead body; electrically coupling the plurality of electrodes to the plurality of terminals using a plurality of conductors disposed within the lead body, and disposing at least one capsule along the distal end of the lead body and relative to the electrode array to indicate, when viewed fluoroscopically, an orientation of the electrode array. Each of the at least one capsule includes an x-ray fluorescent material.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and leads and methods of making and using the systems and leads. The present invention is also directed to electrical stimulation leads having electrodes and x-ray fluorescent capsules for identifying the orientation of one or more of the electrodes, as well as methods of making and using the leads, electrodes, and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. Examples of devices and leads, including leads which can be modified to include the x-ray fluorescent capsules described below, include those described in U.S. Pat. Nos. 7,809,446; 8/295,944; and U.S. Patent Application Publications Nos. 2007/0150036; 2009/0187222; 2009/0276021; 2010/0076535; 2010/0268298; 2011/0005069; 2011/0130803; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; and 2012/0203321; and U.S. patent application Ser. No. 12/177,823; and U.S. Provisional Patent Application Ser. Nos. 61/170,037; 61/022,953; 61/316,759; and 61/591,046, all of which are incorporated herein by reference.

Figure 1:
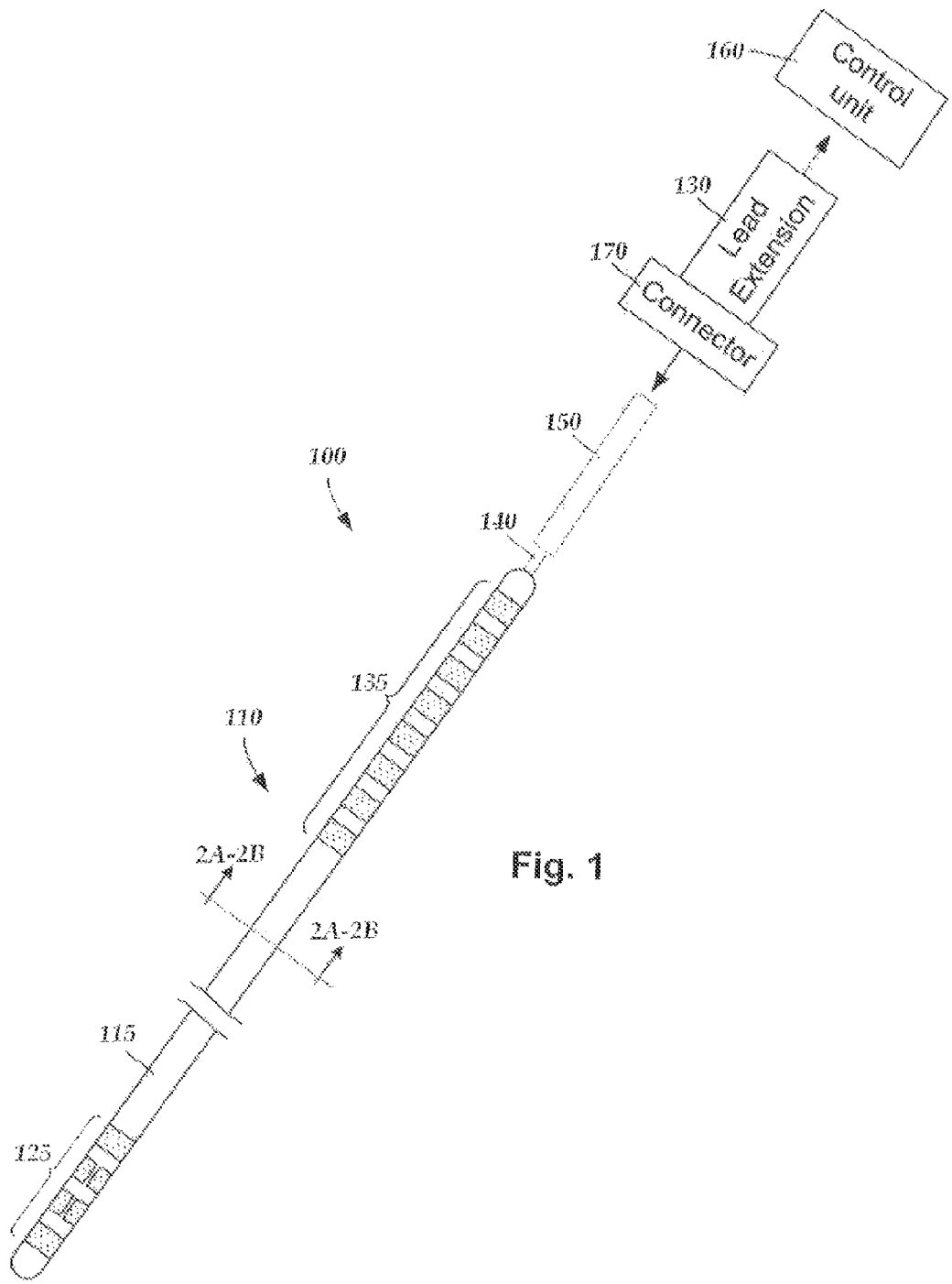
FIG. 1 is a schematic side view of one embodiment of a brain stimulation system that includes a lead with a lead body, a lead extension, and a control unit, according to the invention.

FIG. 1 illustrates one embodiment of an electrical stimulation system 100 for brain stimulation. The electrical stimulation system 100 includes a lead 110 having a lead body 115, a plurality of electrodes 125 disposed at least partially about a circumference of the lead body 115, a plurality of terminals 135, a lead extension 130 for connection of the electrodes 125 to a control unit 160, and a stylet 140 for assisting in insertion and positioning of the lead 110 in the patient's brain, it may be advantageous to include the lead extensions 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140.

The control unit 160 is typically an implantable pulse generator that can be implanted into a patient's body, for example, below the patient's clavicle area. The pulse generator can have eight stimulation channels which may be independently programmable to control the magnitude of the current stimulus from each channel. In some eases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110.

In one example of operation, access to the desired stimulation location in the brain can be accomplished by drilling a hole in the patient's skull or cranium with a cranial drill (commonly referred to as a "burr" or "bur"), and coagulating and incising the dura mater, or brain covering. The lead 110 can be inserted into the cranium and brain tissue with the assistance of the stylet 140. The lead 110 can be guided to the target stimulation location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician, may observe the muscle and provide feedback.

The lead 110 for deep brain stimulation can include stimulation electrodes, recording electrodes, or both, in at least some embodiments, the lead 110 has a cross-sectional diameter of no more than 1.5 mm and may be in the range of no less than 0.5 mm and no greater than 1.5 mm. In at least some embodiments, the lead 110 is rotatable so that the stimulation electrodes 125 can be aligned with the target neurons after the neurons have been located using the recording electrodes. The stimulation electrodes 125 may be disposed on the circumference of the lead 110 to stimulate the target neurons. The stimulation electrodes 125 may be ring-shaped so that current projects from each electrode equally in every direction at any given length along the axis of the lead. To achieve current steering, segmented electrodes can be utilized as described in, for example, U.S. patent application Ser. Nos. 12/177,823; 12/237,888; 12/356,480; 12/427,935; 12/498.650; 12/761,622; 12/945,623; 12/945,657; 12/946,659; 12/946,687; 12/966,740; 13/048,779; 13/159,040; 13/176,595; 13/198,035; 13/226,159; 13/275,112; 13/363,059; 13/368,733; 13/368,982; and 13/369,013; and U.S. Provisional Patent Application Ser. Nos. 61/170,037; 61/023,953; 61/316,759; and 61/591,046, all of which are incorporated, herein by reference. Though the following description discusses stimulation electrodes, it will be understood that all configurations of the stimulation electrodes discussed may be utilized in arranging recording electrodes as well.

The stimulation electrodes 125 may be made using a metal, alloy, conductive oxide, or my other suitable conductive material. Examples of suitable materials include, but are not limited to, platinum, platinum iridium alloy, palladium, palladium-rhodium alloy, or titanium. Preferably, the stimulation electrodes 125 are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a first period of time and a cathode for a second, non-overlapping period of time. In other embodiments, the identity of a particular electrode or electrodes as an anode or cathode might be fixed.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear.

Figure 2A:
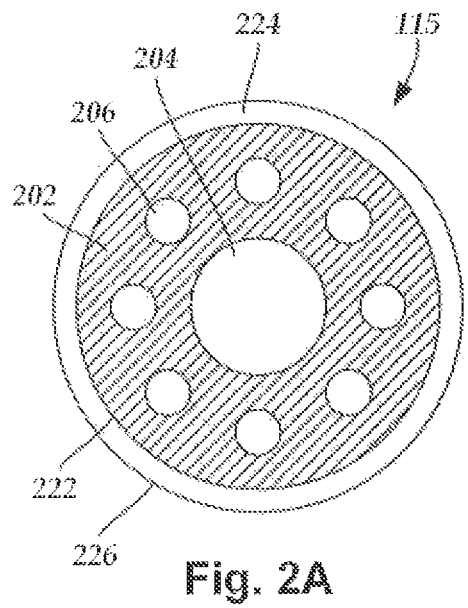
FIG. 2A is a transverse cross-sectional view of one embodiment of a portion of the lead body of FIG. 1, the lead body including a multi-lumen conductor guide that defines a central lumen and a plurality of conductor lumens arranged around the central lumen, according to the invention.
Figure 2B:
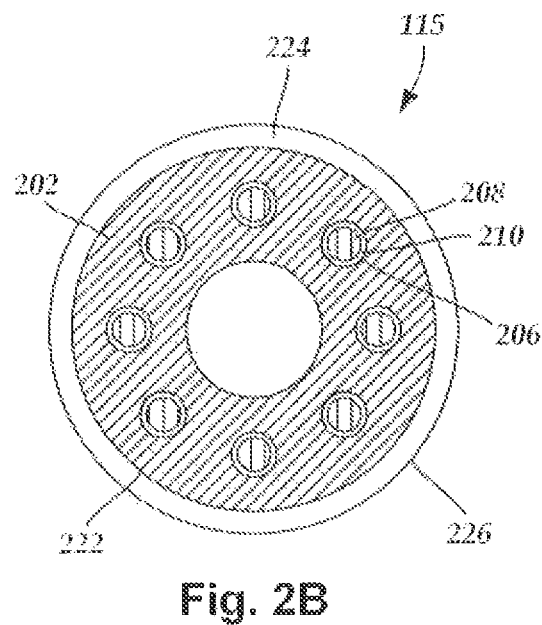
FIG. 2B is a transverse cross-sectional view of one embodiment of conductors disposed in each of a plurality of conductor lumens of the multi-lumen conductor guide of FIG. 2A, according to the invention.

Turning to FIGS. 2A-2B, in at least some embodiments the lead body 115 may include strain relief to modulate deflection of one or more portions of the lead in response to bending of one or more portions of the lead. Examples of lead bodies with strain relief are found in, for example, U.S. Patent Application Ser. No. 61/494,247 and U.S. Patent Application Ser. No. 61/554,861, each of which is incorporated herein by reference in its entirety. Strain relief may be provided in any suitable manner. In some embodiments, the lead includes a lead body with one or more elongated multi-lumen conductor guides. In which case, the one or more multi-lumen conductor guides may include conductor lumens with one or more helical sections that provide strain relief.

In at least some embodiments, the lead body 115 includes an elongated multi-lumen conductor guide having multiple conductor lumens arranged about a central lumen. In at least some embodiments, the conductor lumens are arranged about the central lumen such that there are no other lumens extending along the multi-lumen conductor guide between the central lumen and each of the multiple conductor lumens. The conductor lumens include at least one helical section forming an enclosed pathway around at least a portion of the central lumen. In some embodiments, the conductor lumens are each configured and arranged to receive a single conductor. In other embodiments, at least one of the conductor lumens is configured and arranged to receive multiple conductors.

FIG. 2A is a transverse cross-sectional view of one embodiment of a portion of the lead body 115. The lead body 115 includes an elongated multilumen conductor guide 202 defining a central lumen 204 and a plurality of conductor lumens, such as conductor lumen 206, disposed around the central lumen 204. The central lumen 204 may be configured and arranged to receive a stylet, such as the stylet (140 in FIG. 1). As discussed above, the stylet 140 can be used for assisting in insertion and positioning of the lead in the patient's brain.

FIG. 2B is a transverse cross-sectional view of one embodiment of conductors, such as conductor 208, disposed in conductor lumens 206. In at least some embodiments, insulation 210 is disposed around the conductors 208 to prevent short-circuiting of the conductors 208. The multi-lumen conductor guide 202 may extend an entire longitudinal length of the lead, body 115 from the electrodes 125 to the terminals 135. The conductor lumens 206 can have any suitable cross-sectional shape (e.g., round, oval, rectangular, triangular, or the like).

The central lumen 204 and the plurality of conductor lumens 206 can be arranged in any suitable manner. In preferred embodiments, the conductor lumens 206 are disposed in the multi-lumen conductor guide 202 such that the conductor lumens 206 are peripheral to the central lumen 204. In at least some embodiments, the lead body 115 may include one or more outer coatings of material 224 disposed over the outer surface 222 of multi-lumen conductor guide 202. In at least some embodiments, the one or more outer coatings 224 provide the lead body 115 with an isodiametric outer surface 226.

In at least some embodiments, at least one of the conductor lumens 206 is configured and arranged to concurrently receive two or more conductors 208. In some embodiments, at least one of the conductor lumens 206 can be configured and arranged to receive a different number of conductors than at least one other of the conductor lumens 206. When the conductor lumens 206 are configured and arranged to receive a plurality of conductors, the conductor lumens 206 can be arranged in any suitable configuration.

The electrodes 125 are coupled to one end of the multi-lumen conductor guide 202 and the terminals 135 are coupled to the opposing end of the multi-lumen conductor guide 202. In at least some embodiments, outer portions of the multi-lumen conductor guide 202 are ablated at the ends to expose the conductor lumens 206. In which case, the electrodes 125 may be disposed over the ablated portion at one end of the multi-lumen conductor guide 202, and the terminals 135 may be disposed over the ablated portion at the opposing end of the multi-lumen conductor guide 202 and be electrically coupled to conductors 208 extending within the exposed conductor lumens 206. In at least some embodiments, spacers are used to separate adjacent electrodes 125 (and adjacent terminals 135) from one another. In at least some embodiments, die spacers are isodiametric with the electrodes 125 (and terminals 135). In at least some embodiments, the lead body 115, the spacers, the electrodes 125, and the terminals 135 are isodiametric with one another.

Figure 3:
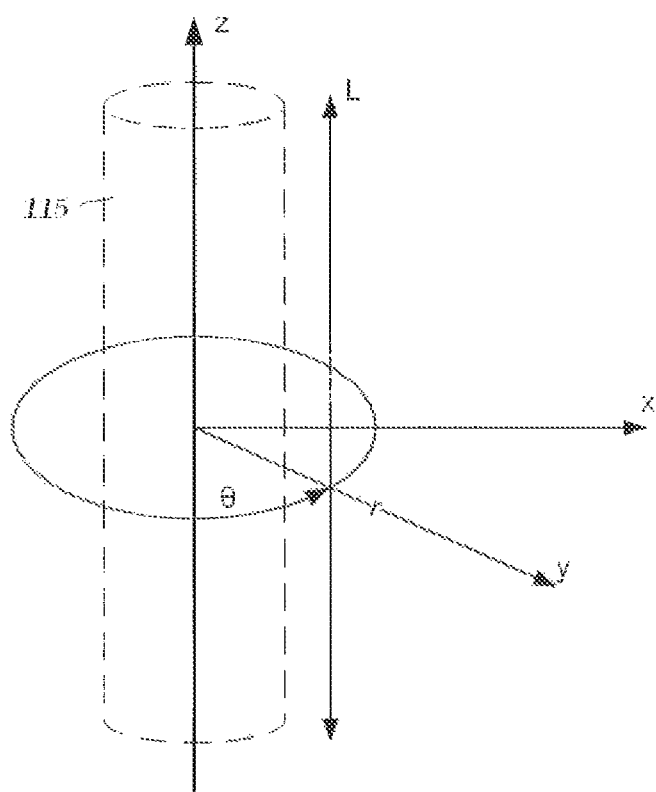
FIG. 3 is a schematic diagram of one embodiment of radial current steering along various electrodes disposed along the longitudinal length of the lead body of FIG. 1, according to the invention.

Turning to FIG. 3, it may be advantageous to stimulate patient tissue using segmented electrodes disposed around the circumference of the lead. Such electrodes enable directed stimulation (e.g., current steering), where stimulation energy is directed to discrete regions of patient tissue adjacent to the lead, while not stimulating other regions of adjacent patient tissue. In some instances, it may be desirable to stimulate a specific region of patient tissue ("a target stimulation region") disposed around the circumference of the lead without undesirably stimulating other patient tissue disposed about the circumference of the lead. In which case, the targeted stimulation region can be stimulated by rotating the lead until the directed stimulation energy propagating from one or more of the segmented electrodes is directed to the target stimulation region.

FIG. 3 is a schematic diagram to illustrate radial current steering along electrodes disposed along the longitudinal length of the lead body 115. While conventional lead configurations with ring electrodes are only able to steer current along the length of the lead (the z-axis), the segmented electrode configuration is capable of steering current in the x-axis, y-axis, as well as the x-axis. Thus, the centroid of stimulation may be steered in any direction in the three-dimensional space surrounding the lead body 115. In some embodiments, the radial distance, r, and the angle θ around the circumference of the lead body 115 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes enables the centroid of stimulation to be shifted to a variety of different locations along the lead body 115.

Figure 4:
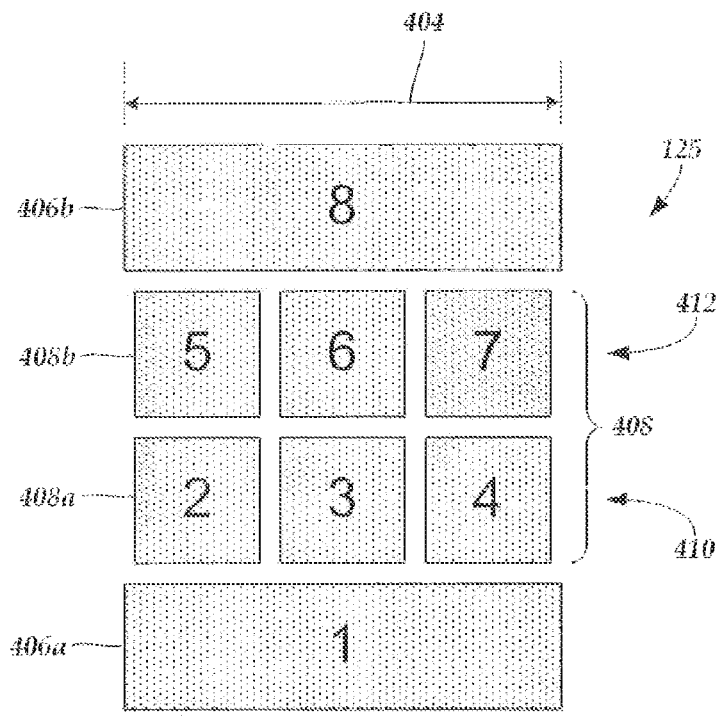
FIG. 4 is a schematic side view of one embodiment of the electrodes of FIG. 1 unrolled into a flat configuration for illustration purposes, according to the invention.

Turning to FIG. 4, the stimulation electrodes 125 may be disposed on the lead 100 in any suitable configuration. FIG. 4 illustrates one embodiment of the electrodes 125 unrolled from a cylindrical shape (see e.g., FIG. 1) so that the electrodes 125 are laid out flat, for clarity of illustration of the configuration of the electrodes. In other words. FIG. 4 is a two-dimensional version of the three-dimensional electrode configuration of FIG. 1.

In FIG. 4, the electrodes 125 are shown flattened such that the length indicated by arrow 404 is equal to the circumference of the lead body 115 (see e.g., FIG. 1). The electrodes 125 of FIG. 4 include two ring electrodes 406a and 406b flanking a plurality of segmented electrodes 408, such as segmented electrodes 408a and 408b arranged into two sets, or levels 410 and 412. The electrodes 125 may include any number of ring electrodes, or even a single ring electrode. For example, the electrodes 125 may include one ring electrode, two ring electrodes, three ring electrodes or four ring electrodes. In some embodiments, the electrodes 125 include five, six, seven or eight ring electrodes.

In at least some embodiments, the ring electrodes 406a, 406b are substantially cylindrical and wrap around an entire circumference of the lead body 115. In at least some embodiments, the outer diameter of the ring electrodes 406a, 406b is substantially equal to the outer diameter of the lead body. Furthermore, the width of ring electrodes 406a, 406b may vary according to the desired treatment and the location of the target neurons. In some embodiments the width of the ring electrode 406a is less than or equal to the diameter of the ring electrode 406b. In other embodiments, the width of the ring electrode 406a is greater than the diameter of the ring electrode 406b.

The electrodes 125 also include the segmented electrodes 408. The electrodes 125 may include any number of segmented electrodes 408 collectively wrapped around the circumference of the lead body 115. In some embodiments, the segmented electrodes 408 are grouped into sets of segmented electrodes, such as sets 410 and 412, where each set is configured for disposing around the circumference of the lead body 115 at or near a particular longitudinal position.

The electrodes 125 may include any number of sets of segmented electrodes 408. In at least some embodiments, the electrodes 125 include one, two, three, four, five, six, seven, eight, or more sets of segmented electrodes 408. In at least some embodiments, each set of segmented electrodes contains the same number of segmented electrodes 408. In some embodiments, each set of segmented electrodes contains three segmented electrodes 408. In at least some other embodiments, each set of segmented electrodes contains two, four, five, six, seven or eight segmented electrodes 408. The segmented electrodes 408 may vary in size and shape. In some embodiments, the segmented electrodes 408 are all of the same size, shape, diameter, width, area or any combination thereof.

Any combination of ring electrodes 406a, 406b and segmented electrodes 408 may be disposed on the lead body 115. For example, in FIG. 4 the lead body 115 includes the ring electrode 406a, two sets of segmented electrodes; each set formed of three segmented electrodes 408, and the ring electrode 406b. This configuration may simply be referred to as a 1-3-3-1 configuration. It may be useful to refer to the electrodes 125 with this shorthand notation. Other eight-electrode configurations include, for example, a 2-2-2-2 configuration, where four sets of segmented electrodes 408 are disposed on the lead, and a 4-4 configuration, where two sets of segmented electrodes, each having four segmented electrodes 408, are disposed on the lead. In some embodiments, the lead upon which the electrodes are disposed includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 5:
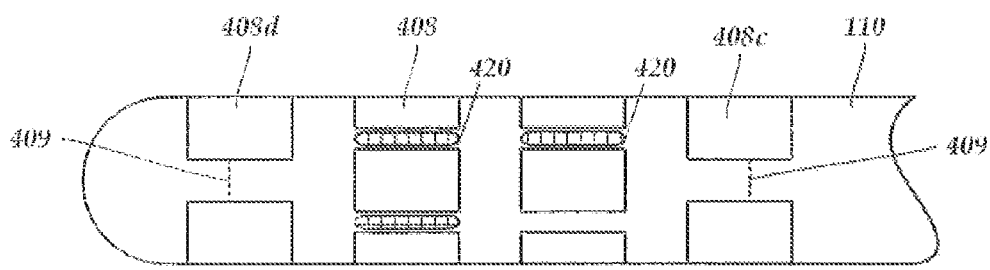
FIG. 5 is a schematic side view of one embodiment of a distal portion of a lead, with x-ray fluorescent capsules; according to the invention.

In some embodiments, two or more segmented electrodes may be electrically coupled together by, for example, a wire or other conductor attached to the coupled segmented electrodes or by coupling these segmented electrodes to the same terminal. FIG. 5 illustrates one embodiment of a 2-3-3-2 electrode arrangement where, in at least some embodiments, the two electrodes 408c in the proximal set are electrically coupled together and the two electrodes 408d in the distal set are electrically coupled together by conductors 409. This allows these ten segmented electrodes 408, 408a, 408b to be coupled to eight independent terminals (not shown).

In at least some embodiments, each set of segmented electrodes 408 may be disposed around the circumference of the lead body 115 to form a substantially or approximately cylindrical shape around the lead body 115. The spacing of the segmented electrodes 408 around the circumference of the lead body 115 may vary. In at least some embodiments, equal spaces, gaps, or cutouts are disposed between each segmented electrode 408 disposed around the circumference of the lead body 115 (i.e., each segmented electrode 408 within a given set). In other embodiments, the spaces, gaps, or cutouts between segmented electrodes 408 may differ in size or shape. In other embodiments, the spaces, gaps, or cutouts between segmented electrodes 408 may be uniform for a particular set of segmented electrodes 408 or for all sets of segmented electrodes 408.

When the segmented electrodes 408 are disposed on the lead body 115, the segmented electrodes 408 may be positioned in irregular or regular intervals around the circumference of the lead body 115 such that each of the different segmented electrodes 408 extends around a different portion of the circumference. When the segmented electrodes 408 are disposed on the lead body 115, for example in a 1-3-3-1 or 2-3-3-2 configuration, each of the segmented electrodes 408 extends partially around the circumference of the lead body 115 such that the segmented electrodes collectively extend no more than 98%, 96%, 94%, 92%, 90%, 80%, 70%, 60%, 50%, 40%, 30%, or 20% around the circumference of the lead body 115.

Turning briefly back to FIG. 3, the centroid of stimulation can be shifted within each set 410, 412 along the length of the lead body 115. The use of multiple sets of segmented electrodes at different levels along the length of the lead allows for three-dimensional current steering, in some embodiments, the sets of segmented electrodes are shifted collectively (i.e., the centroid of simulation is similar at each level along the length of the lead body 115). In at least some other embodiments, each set of segmented electrodes is controlled independently. It will be understood that different stimulation profiles may be produced by varying the number of segmented electrodes within each set 410. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Regardless of the type of electrodes used, proper placement of the lead may be important in providing proper and adequate treatment. For example, in some cases the target stimulation region may be located on one side of a plane extending through the longitudinal length of the lead. In other cases, the target stimulation region may be located at a plane that is offset at some angle from the longitudinal length of the lead. Thus, it is desirable to be able to rotate the lead such that the appropriate one or more electrodes are in rotational alignment with the target stimulation region. It may, accordingly, be advantageous to be able to determine the circumferential position of the electrodes on the lead within the brain.

Turning back to FIG. 4, the electrodes 125 are shown numbered from 1 to 8. In at least some embodiments, when the electrodes 125 are disposed on the lead body 115 (see e.g., FIG. 1), each of die electrodes 125 is coupled to a different terminal of the plurality of terminals 135. In which case, for example, the ring electrode 406*a*, which is numbered "1," may be electrically coupled a particular terminal of the plurality of terminals 135. Similarly, the ring electrode 406*b*, which is numbered "8," may be electrically coupled a different particular terminal of the plurality of terminals 135. Likewise, each of the segmented electrodes 408 may be electrically coupled to a different terminal of the plurality of terminals 135.

In at least some embodiments, the terminals 135 are also numbered to correspond to particular electrodes 125. For example, in at least some embodiments the terminals are numbered 1-8 such that, the proximal-most terminal of the plurality of terminals is numbered "1," and the next most proximal terminal is numbered "25" and so on. In at least some embodiments, the electrode "1" electrically couples with the terminal "1," the electrode "2" electrically couples with the terminal "2," and so on.

In at least some embodiments, the electrodes 125 are arranged such that when the electrodes 125 are disposed on the lead body (see e.g., FIG. 1), some of the segmented electrodes 408 align with one another along a longitudinal length, of the lead body 115. For example, when the electrodes 125 are disposed on the lead body 115, the segmented electrode labeled "2" aligns along the longitudinal length of the lead body 115 with the segmented electrode labeled "5." Similarly, the segmented electrode labeled "3" aligns with the segmented electrode labeled "6" and the segmented electrode labeled "4" aligns with the segmented electrode labeled "7."

It is generally desirable that the orientation (particularly, the rotational orientation) of the electrode array and, in particular, the segmented electrodes be known so that the practitioner can select appropriate electrodes (e.g., electrodes facing the tissue to be stimulated) to provide stimulation. This can allow a practitioner to identify electrodes that are rotationally aligned with the tissue to be stimulated. X-ray fluorescent capsules can be placed near selected electrodes to facilitate identification of the orientation (e.g., rotational orientation/rotational alignment) of the distal array of segmented electrodes under a fluoroscope or other x-ray device. Accordingly, a lead can include one or more capsules filled with an x-ray fluorescent material disposed relative to the array of electrodes to assist in indicating the orientation (e.g., rotational orientation/rotational alignment) of the electrode array. The capsule(s) are embedded in the lead at one or more specific locations so that the capsule(s), along with the electrodes on tire lead body, provide a fluoroscopic image of the lead that identifies the orientation (e.g., rotational orientation/rotational alignment) of the lead. As an example, the capsule(s) may be filled with sodium iodide having traces of thallium (NaI(Tl)). NaI(Tl) emits a blue glow in the presence of x-rays.

Figure 6:
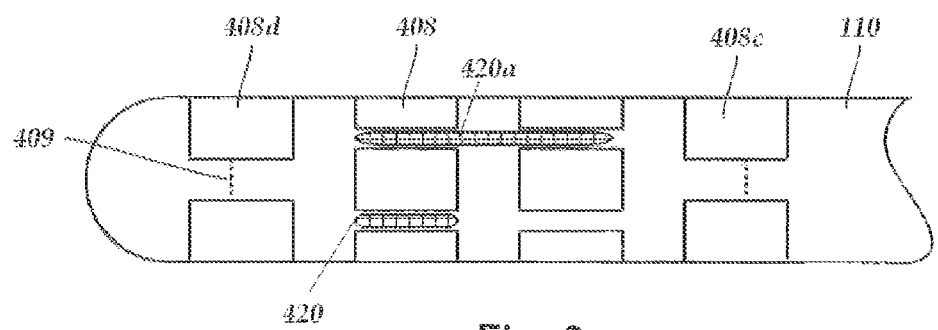
FIG. 6 is a schematic side view of a second embodiment of a distal portion of a lead with x-ray fluorescent capsules; according to the invention.
Figure 7:
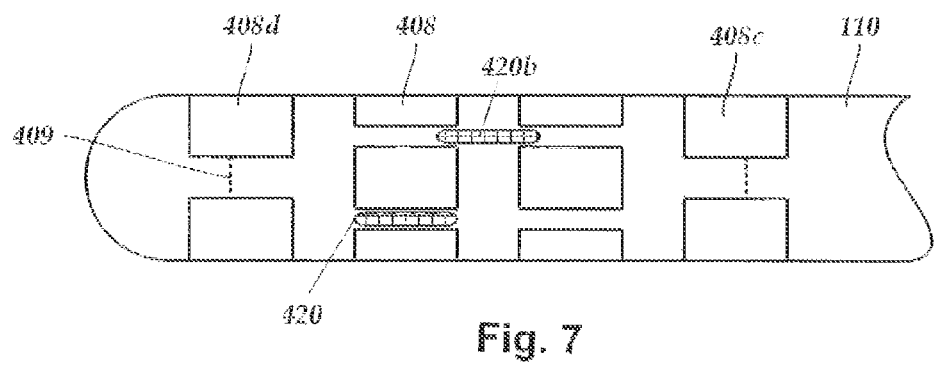
FIG. 7 is a schematic side view of a third embodiment of a distal portion of a lead with x-ray fluorescent capsules; according to the invention.

FIG. 5 illustrates one embodiment of a lead 110 with sets of segmented electrodes 408 and one or more capsules 420 that contain an x-ray fluorescent material, such as sodium iodide with traces of thallium (NaI(Tl)). The capsules 420 are placed at specific locations relative to the array of electrodes 408 as illustrated in FIG. 5. The capsules 420 can be placed at any location or in any orientation that will help in determining the orientation (e.g., rotational orientation/rotational alignment) of the array of electrodes 408 on the lead 110. In FIG. 5, there are two capsules between three adjacent electrodes of a distal set of three segmented electrodes and one capsule between two adjacent electrodes of a proximal set of three segmented electrodes. It will be understood that other arrangements of capsules may be used to indicate the orientation (e.g., rotational orientation/rotational alignment) of the electrodes of the array. For example, in the embodiment illustrated in FIG. 6, one capsule 420*a* is particularly long so that it extends between both sets of three segmented electrodes. In the embodiment illustrated in FIG. 7, one capsule 420*b* is disposed partially between electrodes in both sets of three segmented electrodes, but is not as long as the capsule 420*a* in FIG. 6. In at least some embodiments, the capsule 420*b* is the same size as the other capsule(s) 420. Thus, as illustrated in FIGS. 5-7 a capsule 420 may be disposed only between electrodes 408 of a particular set of segmented electrodes. Alternatively or additionally, a capsule 420*a*, 420*b* may be disposed between electrodes 408 of two or more sets of segmented electrodes.

The capsules 420 can be fabricated through a molding process and can be of any shape or size. For example, the shape of the capsules 420 may be oval, circular, square, triangular, or of any regular or irregular shape. A variety of different capsule arrangement can be fabricated. For example, the capsules may have a polymer skin with fluid or solid x-ray fluorescent material disposed within the capsule. For example, the capsule 420 can have a silicone or polyurethane skin with NaI(Tl) in fluid or solid form disposed within the skin. As another example, the capsules 420 may be made of a polymer matrix with an x-ray fluorescent material embedded in the matrix. For example, the polymer matrix may be silicone or polyurethane with NaI(Tl), barium sulphate, or titanium dioxide embedded in the matrix.

The capsules 420 can be disposed within or on the lead in any manner and during any suitable portion of the lead manufacturing process. For example, the capsules 420 may be molded with the lead during manufacture, or inserted into the lead through an opening or through an end of the lead, or adhesively attached to the surface of the lead, or attached to the lead by any other suitable attachment, mechanism.

In one embodiment, the lead body 115 may also include indicia (not shown) that assist in determining the orientation of the electrode array. The indicia may include symbols, words, or any kind of marking that is visible under a fluoroscope or by the naked eye or both.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent is:

1. An implantable lead for an electrical stimulation system, the lead comprising:
   a lead body having a distal end, a proximal end, a longitudinal axis, and a circumference;
   a plurality of electrodes disposed along the distal end of the lead body in an electrode array, the plurality of electrodes comprising a plurality of segmented electrodes, wherein each of the plurality of segmented electrodes extends partially around the circumference of the lead body;
   a plurality of terminals disposed along the proximal end of the lead body;
   a plurality of conductors electrically coupling the plurality of electrodes to the plurality of terminals; and
   at least one capsule comprising a polymer skin and an x-ray fluorescent material disposed within the polymer skin, wherein the at least one capsule is disposed along the distal end of the lead body relative to the electrode array to indicate, when viewed fluoroscopically, an orientation of the electrode array.

2. The lead of claim 1, wherein the at least one capsule comprises a plurality of capsules.

3. The lead of claim 1, wherein the x-ray fluorescent material comprises sodium iodide and thallium.

4. The lead of claim 1, wherein the plurality of segmented electrodes are arranged into a plurality of sets of segmented electrodes, wherein each set comprises a plurality of the segmented electrodes and the segmented electrodes of each set are disposed at a same longitudinal position along the distal end of the lead body.

5. The lead of claim 4, wherein the at least one capsule comprises a plurality of capsules and the plurality of sets of segmented electrodes comprises a first set of segmented electrodes disposed at a first longitudinal position along the distal end of the lead body and a second set of segmented electrodes disposed at a second longitudinal position along the distal end of the lead body.

6. The lead of claim 5, wherein at least two capsules of the plurality of capsules are disposed so that, when viewed fluoroscopically, the at least two capsules appear at least partially disposed between segmented electrodes of the first set of segmented electrodes.

7. The lead of claim 6, wherein the at least two capsules of the plurality of capsules are disposed so that, when viewed fluoroscopically, the at least two capsules appear entirely disposed between segmented electrodes of the first set of segmented electrodes.

8. The lead of claim 5, wherein at least one capsule of the plurality of capsules is disposed so that, when viewed fluoroscopically, the at least one capsule appears at least partially disposed between segmented electrodes of the second set of segmented electrodes and at least partially disposed between segmented electrodes of the first set of segmented electrodes.

9. The lead of claim 1, wherein each of the at least one capsule has a long axis arranged longitudinally parallel to a longitudinal axis of the lead.

10. The lead of claim 1, wherein the at least one capsule is disposed within the lead body.

11. The lead of claim 1, wherein the polymer skin comprises silicone or polyurethane.

12. The lead of claim 1, wherein the x-ray fluorescent material is a fluid.

13. A stimulation system comprising:
   the lead assembly of claim 1;
   a control unit coupleable to the lead, the control unit configured and arranged for providing stimulation to the plurality of electrodes of the lead.

14. A method for making an implantable lead, the method comprising:
   disposing a plurality of electrodes along a distal end of a lead body and arranged in an electrode array, the plurality of electrodes comprising a plurality of segmented electrodes, wherein each of the plurality of segmented electrodes extends partially around a circumference of the lead body;
   disposing a plurality of terminals along a proximal end of the lead body;
   electrically coupling the plurality of electrodes to the plurality of terminals using a plurality of conductors disposed within the lead body; and
   disposing at least one capsule along the distal end of the lead body and relative to the electrode array to indicate, when viewed fluoroscopically, an orientation of the electrode array, each of the at least one capsule comprising a polymer skin and an x-ray fluorescent material disposed within the polymer skin.

15. The method of claim 14, wherein disposing at least one capsule comprises molding the at least one capsule into the lead body.

16. The method of claim 14, wherein disposing at least one capsule comprises adhesively attaching the at least one capsule to the lead body.

17. The method of claim 14, wherein the plurality of segmented electrodes are arranged into a plurality of sets of segmented electrodes, wherein each set comprises a plurality of the segmented electrodes and the segmented electrodes of each set are disposed at a same longitudinal position along the distal end of the lead body,
   wherein the at least one capsule comprises a plurality of capsules and the plurality of sets of segmented electrodes comprises a first set of segmented electrodes disposed at a first longitudinal position along the distal end of the lead body and a second set of segmented electrodes disposed at a second longitudinal position along the distal end of the lead body, and
   wherein disposing at least one capsule comprises disposing at least two capsules of the plurality of capsules within the lead body and along the lead body so that, when viewed fluoroscopically, the at least two capsules appear at least partially disposed between segmented electrodes of the first set of segmented electrodes.

18. The method of claim 17, wherein disposing at least one capsule further comprises disposing at least one capsule of the plurality of capsules so that, when viewed fluoroscopically, the at least one capsule appears at least partially disposed between segmented electrodes of the second set of segmented electrodes.

19. The method of claim 14, further comprising forming the at least one capsule by molding the at least one capsule.

20. The method of claim 14, wherein the x-ray fluorescent material comprises sodium iodide and thallium.

* * * * *